United States Patent [19]

Speert et al.

[11] Patent Number: 5,514,665
[45] Date of Patent: May 7, 1996

[54] METHOD OF PREVENTING OR REDUCING THE RISK OF INFECTION BY BACTERIAL PATHOGENS UTILIZING SIMPLE AND CONJUGATED DEXTRANS

[75] Inventors: David P. Speert, Vancouver, Canada; Thomas C. Usher, Nassau, Bahamas

[73] Assignee: University of British Columbia, Vancouver, Canada

[21] Appl. No.: 317,228

[22] Filed: Oct. 3, 1994

Related U.S. Application Data

[63] Continuation-in-part of Ser. No. 175,956, Dec. 30, 1993, abandoned.

[51] Int. Cl.⁶ ............................................. A61K 31/715
[52] U.S. Cl. .................. 514/53; 424/43; 424/45; 424/46; 424/464; 514/23; 514/54; 514/57; 514/58; 514/59; 514/56; 514/849; 514/850; 514/851; 514/853
[58] Field of Search .................... 424/43, 45, 46, 424/464; 514/23, 54, 57, 58, 59, 56, 849, 850, 851, 853

[56] References Cited

U.S. PATENT DOCUMENTS

| | | | |
|---|---|---|---|
| 3,917,819 | 11/1975 | Yoshioka et al. | 424/43 |
| 4,141,746 | 2/1978 | Schweiger | 536/59 |
| 4,177,345 | 12/1979 | Schweiger | 536/59 |
| 4,238,482 | 12/1980 | Peyman et al. | 536/112 |
| 4,496,689 | 1/1985 | Mitra | 514/59 |
| 4,501,729 | 2/1985 | Boucher et al. | 514/255 |
| 4,668,508 | 5/1987 | Grollier et al. | 424/70 |
| 4,826,679 | 5/1989 | Roy | 514/562 |
| 4,840,941 | 6/1989 | Ueno et al. | 514/59 |
| 4,866,072 | 9/1989 | Edwards et al. | 514/851 |
| 4,920,194 | 4/1990 | Feller et al. | 530/385 |
| 4,966,894 | 10/1990 | Herr et al. | 514/56 |
| 4,973,580 | 11/1990 | Mascellani et al. | 514/54 |
| 4,981,841 | 1/1991 | Gibson | 514/21 |
| 5,013,724 | 5/1991 | Petitou et al. | 514/54 |
| 5,037,810 | 8/1991 | Saliba, Jr. | 514/56 |
| 5,055,301 | 10/1991 | Voigt et al. | 514/59 |
| 5,071,969 | 12/1991 | Boeckel et al. | 514/54 |
| 5,089,479 | 2/1992 | Krivan et al. | 514/25 |
| 5,100,879 | 3/1992 | Ueno et al. | 514/59 |
| 5,135,919 | 8/1992 | Folkman | 514/56 |
| 5,141,928 | 8/1992 | Goldman | 514/54 |
| 5,157,024 | 10/1992 | Gordon | 514/23 |
| 5,164,378 | 11/1992 | Conti et al. | 514/56 |
| 5,217,715 | 6/1993 | Krivan et al. | 536/53 |
| 5,221,669 | 6/1993 | Anand et al. | 514/58 |
| 5,240,710 | 8/1993 | Bar-Shalom et al. | 424/401 |
| 5,288,704 | 2/1994 | Ungheri et al. | 514/12 |
| 5,292,498 | 3/1994 | Boucher | 514/255 |
| 5,384,128 | 1/1995 | Meezan et al. | 424/450 |

FOREIGN PATENT DOCUMENTS

| | | |
|---|---|---|
| 0177783 | 4/1986 | European Pat. Off. . |
| 0126043 | 11/1994 | European Pat. Off. . |
| 9115216 | 10/1991 | WIPO . |
| 9307178 | 4/1993 | WIPO . |
| 9308810 | 5/1993 | WIPO . |
| 9324505 | 12/1993 | WIPO . |

*Primary Examiner*—Ronald W. Griffin
*Attorney, Agent, or Firm*—Choate, Hall & Stewart

[57] ABSTRACT

Methods for reducing the risk of or preventing infections by bacterial pathogens in vivo. In particular, a method for reducing the risk of *P. aeruginosa* infection in vivo in compromised hosts such as cystic fibrosis patients. The methods involve the use of dextran or dextran sulphate as the active ingredient.

17 Claims, 5 Drawing Sheets

METHOD OF PREVENTING OR REDUCING THE RISK OF INFECTION BY BACTERIAL PATHOGENS UTILIZING SIMPLE AND CONJUGATED DEXTRANS

CROSS-REFERENCE TO RELATED APPLICATIONS

The present application is a continuation-in-part of application Ser. No. 08/175,956 filed Dec. 30, 1993, now abandoned.

FIELD OF THE INVENTION

The present invention relates to a novel therapy for reducing the risk of acquiring bacterial infections by administering a pharmaceutical composition having simple or conjugated dextrans as active ingredient.

BACKGROUND OF THE INVENTION

Humans are susceptible to infection by a variety of pathogenic bacteria. Such infections pose a significant health risk for the human population in general. The human respiratory tract serves as a major portal for the opportunistic entry of bacterial pathogens into the human body. Once established and having multiplied within the respiratory tract, a bacterial pathogen may have severe localised effects or may further affect other vital bodily functions.

Pathogen entry into the respiratory tract can be reduced by the activity of the ciliary and mucus producing cells lining the respiratory tract. Individuals whose normal biological defence mechanisms have been compromised suffer from greater susceptibility to opportunistic infection by bacterial pathogens.

Typical examples of human diseases contracted due to the entry of bacterial pathogens into the respiratory system are bronchitis and pneumonia. Numerous bacterial species are known to be the causative agents of both of these diseases. For example, Streptococcus pneumoniae is a common causative agent of pneumonia while bronchitis may be caused by numerous species of Streptococcus or Staphylococcus. For each of these disease examples, establishment of the bacterial pathogen within the respiratory system is facilitated when either the normal ciliary or mucus producing functions of the respective cells is inhibited. As well, contraction of either of these diseases often leads to the further reduction in the functional abilities of the ciliary and mucus producing cells.

There is, therefore, a need to provide a prophylactic therapy to reduce the risk of, or for the prevention of, infection of the respiratory system by bacterial pathogens.

A further example of the debilitating and often lethal effects due to infection by a bacterial pathogen is evident in persons suffering from cystic fibrosis. Cystic fibrosis ("CF") is a congenital metabolic disorder which is common among Caucasians, affecting approximately 1 in 2,000 newborns. The mode of inheritance is generally autosomal recessive, suggesting that about 5% of the normal population carries the defective gene. CF manifests itself in abnormal secretions of the exocrine glands. Excessive viscid mucus causes obstruction of passageways including pancreatic and bile ducts, the intestines, and bronchi.

*Pseudomonas aeruginosa* is the predominant respiratory tract pathogen in patients with cystic fibrosis. Once CF patients acquire a *P. aeruginosa* infection, the infection is rarely, if ever, eradicated and a progressive pulmonary deterioration is initiated, ultimately leading to death. In one study, chronic colonization established in the first five years of life was associated with a 20% survival to 16 years of age, whereas 95% of the patients who remained uncolonized in the first five years of life survived to 16 years of age. Although the extraordinary predisposition of CF patients to colonization and infection with *P. aeruginosa* has been recognized for many years, a satisfactory explanation for this phenomenon remains elusive.

Presently, there are currently no prophylactic measures or treatments that have resulted in the complete eradication of *P. aeruginosa* infections in CF patients.

CF patients with established *P. aeruginosa* infections have been treated by antimicrobial therapy using antibiotics in several prior art therapeutic protocols. However, the complications that have been observed in antibiotic therapy include the following. First, patients with CF dispose of antimicrobial agents more rapidly than do normal individuals, a phenomenon that mandates therapy with higher doses than those normally recommended. Second, strains of *P. aeruginosa* dissociate into multiple phenotypic forms and often with different antimicrobial susceptibility patterns. Third, since the infection is chronic and the infecting strains of *P. aeruginosa* are rarely eradicated, resistance to multiple antimicrobial agents frequently develops. Fourth, therapeutic levels of antimicrobial agents in sputum are difficult to achieve because of poor penetration and inactivation. Fifth, the mucoid exopolysaccharide of mucoid strains appears to present a barrier to penetration of some antibiotics. Finally, allergy to certain antibiotics renders therapy with antibiotics difficult in some patients.

Further, anti-inflammatory agents have been used in the therapy of established *P. aeruginosa* infections in CF patients, as it has been postulated that host-mediated inflammation may be responsible for a large part of the pulmonary damage in the CF lung. Efforts have been made to dampen the inflammatory response in the CF lung by use of a systemic steroidal anti-inflammatory therapy using prednisone. Unfortunately, prednisone therapy carries substantial risks including growth retardation, glucose intolerance and development of cataracts. Preliminary studies are underway to test use of non-steroidal anti-inflammatory agents.

The manner in which *P. aeruginosa* establishes infection in CF patients has been studied. It is understood that a defect in CF host defences against infection must exist a priori, otherwise infection with *P. aeruginosa*, an opportunistic pathogen, would not be possible. Despite extensive investigations, a unifying explanation for the peculiar predisposition of CF patients to infection with *P. aeruginosa* has not been forthcoming.

A range of subtle immunological abnormalities, both primary and secondary, in patients with CF has been identified and incorporated into a feasible pathophysiological scheme. The first of such abnormalities has been identified as the tendency of *P. aeruginosa* to adhere to buccal and respiratory epithelial cells in patients with CF.

*P. aeruginosa* is present in the upper and lower respiratory tracts of most older patients with CF, but it is rarely recovered from healthy individuals. The propensity of *P. aeruginosa* to colonize respiratory epithelia of patients with CF has been attributed to the pathogen's enhanced adhesion to buccal epithelial cells in patients with CF. It has been determined that fibronectin, a glycoprotein which normally coats buccal epithelial cells and prevents adhesion of Gram-negative bacteria, is depleted from the surface of buccal epithelial cells in patients with CF. This provides a possible explanation of the tendency of *P. aeruginosa* to colonize the upper respiratory tract of patients with CF.

Colonization appears to be established in the upper respiratory tract where nonmucoid *P. aeruginosa* adhere to buccal epithelial cells in patients with CF, better than to the same cells in normal individuals. Contamination of the lower airways probably occurs due to spontaneous aspiration of respiratory secretions. Since there is defective mucociliary clearance in patients with CF, such aspirated secretions are not cleared and remain in the lower airways. Once *P. aeruginosa* reaches the lower airways, phagocytosis and killing by macrophages does not occur and a chronic state of infection is established. In this niche, the bacteria are exposed to a new environment which apparently provides the appropriate stimulus for a switch from the nonmucoid to the mucoid phenotype. These mucoid variants may have a survival advantage over nonmucoid strains by virtue of their resistance to phagocytosis and their adhesion to tracheobronchial mucin. Once chronic infection is established, the bacterial density increases dramatically in concert with a down-regulation of toxin production.

As a result of the considerable difficulty and lack of success in treating patients already infected by *P. aeruginosa*, there is a need to provide a prophylactic therapy to reduce the risk of, or for the prevention of, *P. aeruginosa* infection, most importantly in patients with CF. Further, there is a need to provide a therapy to reduce the risk of further such infection during the treatment of a patient who has already been infected.

The present invention provides a method for reducing the risk of or preventing the establishment of infection of the respiratory system by bacterial pathogens by treating individuals with a pharmaceutical composition having as an active ingredient either simple or conjugated polysaccharides. For example, treatment of the buccal or respiratory epithelial cells in a human with either simple or conjugated polysaccharides, administered through a variety of mechanisms, can achieve such a result. Use of the method of the present invention may reduce the risk of colonization of the respiratory tract by a bacterial pathogen. By inhibiting the colonization of the bacterial pathogen, the method of the present invention inhibits the establishment of a diseased state in the individual. As well, the present invention may be used for the treatment of individuals already infected by a bacterial pathogen.

Known references show pharmaceutical compositions comprising polysaccharides or their conjugates, including dextran and dextran sulphate as an active ingredient. Of such references, one has shown that such compositions may be effective in treating against infection of human cells by retroviruses. Ueno et al. ("Ueno"), in U.S. Pat. No. 5,100,879, discloses a method for the disinfection of retroviruses by the application of dextran sulphate in concentrations ranging from 0.01 to 1.0 µg/ml to human T-lymphocytes. The molecular weight of the dextran sulphate may range from 2,000 to 10,000 and have a minimum 5% sulphur content. Treatment of T-cells with dextran alone did not prevent T-cell infection by HTLV-III, a causative agent of AIDS. However, in view of the significant differences between the mechanism of infection of T-cells by retroviruses and infection of the respiratory system by bacterial pathogens, Ueno does not teach or suggest a treatment which would be expected to prevent or reduce the risk of respiratory system infection by bacterial pathogens.

Another reference shows a method of treatment of certain bacterial infections using extremely low concentrations of dextran sulphate. Krivan et al. ("Krivan"), in U.S. Pat. No. 5,089,479, discloses a pharmaceutical composition comprised of either sulphatides, dextran sulphate, sialyloligosaccharides or a mixture thereof, coupled with either a water insoluble or water soluble carrier. The composition is used in a method of removing the mycoplasma pathogen from patients infected with either *Mycoplasma hominus* or *Mycoplasma pneumoniae*. Also disclosed is a method for detecting mycoplasma pathogens from the said groups through the use of an enzyme-dextran sulphate conjugate.

The use of dextran sulphate at the concentrations disclosed in the present invention for reducing the risk of bacterial infection of the respiratory system is not taught or suggested by Krivan as the concentrations of dextran sulphate utilized by Krivan are approximately 1000 times lower than those disclosed herein. Further, Krivan teaches that dextran has no effect on the treatment of Mycoplasma infections and therefore teaches away from the invention disclosed presently.

Methods for treating patients having CF are known. For example, Edwards et al. ("Edwards"), in U.S. Pat. No. 4,866,072, discloses a method for the treatment of CF by the direct administration of the active ingredient nedocromil sodium, in an aqueous solution in aerosol or oral format, to a patient's lung. The active ingredient may range in concentration from 0.1% to 2.0% w/w for aqueous solutions and from 0.5% to 5.0% w/w for pressurized aerosols. Edwards does not contemplate a method for treatment of the respiratory system against bacterial infection.

SUMMARY OF THE INVENTION

According to an aspect of the present invention, there is provided a method for reducing the risk of respiratory system infection by bacterial pathogens which comprises administering to a patient in need of such treatment a pharmaceutical composition comprising an effective amount of a simple or conjugated polysaccharide in admixture with a pharmaceutically acceptable diluent or carrier.

According to another aspect of the present invention, there is provided a method for reducing adhesion of bacterial pathogens to buccal or respiratory epithelial cells in vivo which comprises administering to a patient in need of such treatment a pharmaceutical composition comprising an effective amount of a simple or conjugated polysaccharide in admixture with a pharmaceutically acceptable diluent or carrier.

According to yet another aspect of the present invention, there is provided a method reducing the risk of respiratory tract infection by *P. aeruginosa* in a patient having cystic fibrosis which comprises administering to said patient a pharmaceutical composition comprising an effective amount of dextran sulphate or dextran in admixture with a pharmaceutically acceptable diluent or carrier.

DETAILED DESCRIPTION OF THE INVENTION

Figure 1:
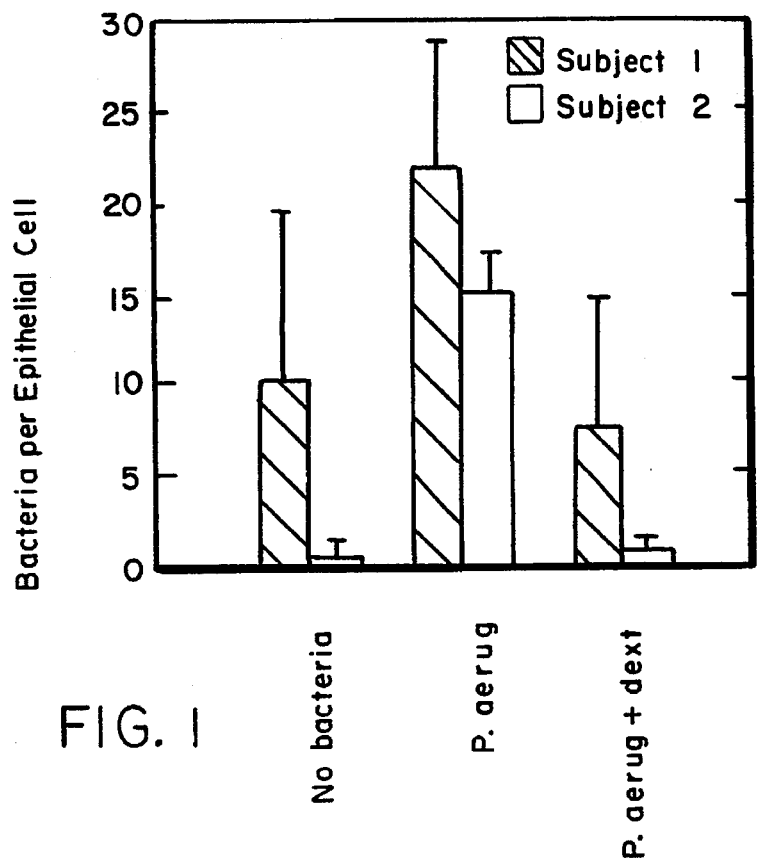
FIG. 1 shows the effect of dextran sulphate on the adhesion of *P. aeruginosa* to buccal epithelial cells.

The inventors have found that dextran or dextran sulphate may be used to reduce the risk of or prevent the adhesion of bacterial pathogens to human respiratory epithelial cells in vitro. From this it can be soundly predicted that polysaccharides such as dextran or dextran sulphate will be effective in reducing the risk of or preventing bacterial pathogens infections in compromised hosts (such as patients with CF) by blocking adhesion (and therefore colonization) to the airway epithelial cells. As well, polysaccharides such as dextran or dextran sulphate would be effective in treating patients already infected with *P. aeruginosa* by reducing the risk of or preventing further infection of such hosts.

Dextran sulphate and its known uses will be recognized by persons skilled in the art. For example, the salts of dextran sulphate, particularly its sodium salt, have been found to be useful as an anti-coagulant, as an anti-lipemic agent and an anti-ulcer agent.

Dextran sulphate is a sulphonated polysaccharide having a wide range of molecular weights. Based upon their studies, the inventors recommend that dextran sulphate having an average molecular weight in the range of 8,000–1,000,000 would be most effective in reducing adhesion of bacterial pathogens to buccal or respiratory epithelial cells.

Experimental results supporting the finding that dextran sulphate reduces the adhesion of bacterial pathogens to buccal epithelial cells are detailed below.

Dextran and its known uses will also be recognized by persons skilled in the art. For example, dextran is known to be useful for the expansion of blood plasma. As well, dextran can act as a blood flow adjuvant due to its ability to prevent erythrocyte aggregation.

Hydrogenated dextran, commonly referred to as simply dextran, is a polymer of glucose, possessing a wide range of molecular weights. Dextran is commercially produced by growing bacterium (*Leuconostoc mesenteroides*) upon a sucrose substrate to yield high molecular weight dextrans. Depolymerization and fractionation of the high molecular weight dextrans will yield lower weight dextrans. Based upon their studies, the inventors recommend that dextran having an average molecular weight in the range of 3,000–1,000,000 would be most effective in reducing adhesion of bacterial pathogens to human respiratory epithelial cells.

Experimental results supporting the finding that dextran reduces the adhesion of bacterial pathogens to buccal epithelial cells are also detailed below.

MATERIALS AND METHODS

Dextran Sulphate

Fresh buccal epithelial cells were obtained from the mouths of two healthy individuals by gently swabbing with alginate swabs. The epithelial cells were suspended in phosphate buffered saline and washed. The cells were divided in tubes into 3 groups for (i) a control; (ii) addition of *P. aeruginosa* and (iii) addition of *P. aeruginosa* and dextran sulphate. *P. aeruginosa* was added to one of the tubes containing the fresh epithelial cells. *P. aeruginosa* and dextran sulphate were added to another tube containing the fresh epithelial cells. The dextran sulphate used is sold under the trademark Usherdex 8 and is a hydrogenated form of dextran sulphate having an average molecular weight of around 8,000. The dextran sulphate solution was 10 mmol strength. All of the tubes were incubated for 60 minutes. At the end of the incubation, the cells were washed and deposited by cytospin on glass slides. The slides were allowed to dry overnight and then stained with Giemsa stain and the bacteria associated with each epithelial cell was determined by visual inspection. Experimental results are demonstrated in FIG. 1.

Referring to FIG. 1, three different conditions are depicted by separate bars on the graph of FIG. 1. The three sets of bars represent the following (from left to right):

(a) the number of bacteria which are normally resident on the epithelial cells from the mouth (i.e. no dextran sulphate or *P. aeruginosa* were added);

(b) the results of the experiment in which *P. aeruginosa* was added; and (c) the results when dextran sulphate (10 mmol) was added along with the *P. aeruginosa* to the epithelial cells.

The adhesion of *P. aeruginosa* to buccal epithelial cells is shown in FIG. 1 by comparing the second and first set of bars. The addition of the bacteria resulted in increased incidence of bacteria per epithelial cell over the number found normally in the mouth. Comparing the third and second set of bars indicates that the treatment of the epithelial cells with dextran sulphate resulted in a reduction in the adhesion of the bacteria to the cells.

Up to 20 mmol (160 mg/ml) dextran sulphate has been used with similar results. As demonstrated in FIG. 1, it has been found that a concentration of 10 mmol (80 mg/ml) is highly effective at interfering with adhesion of *P. aeruginosa* to epithelial cells. Concentrations in the range of 1–50 mmol would be useful for the purpose described herein. It is believed that dextran sulphate concentrations in the range of 10–20 mmol would be most useful in reducing the risk of such *P. aeruginosa* infections.

It is believed that dextran sulphate with a molecular weight in the range of 8,000 to 1,000,000 would be effective in a treatment to reduce the risk of bacterial infections.

In vivo, the dextran sulphate would preferably be administered topically. Dextran sulphate as the active ingredient may be administered topically by gargle, swish and swallow, oral lozenge, aerosol or other such manner. Dextran sulphate and suitable carrier compositions will be understood by those skilled in the art. Preferably, dextran sulphate is delivered to the site of potential adhesion to buccal epithelial cells in concentrations as mentioned above.

Although the foregoing description suggests specific manners of topical administration of dextran sulphate to buccal epithelial cells, it will be understood by persons skilled in the art that other methods of administration are possible.

As a result of its anti-coagulant properties, dextran sulphate may cause some undesired side effects in use. The dextran sulphate used in the present experiment was in its hydrogenated form. Hydrogenation reduces the anti-coagulant effect of the dextran sulphate and is therefore the preferred form as an active ingredient in methods and compositions described herein. It is expected that dextran sulphate in its unhydrogenated form would also be effective for use in a treatment to reduce the risk of such infections.

Preferably, a patient would be treated 2–3 times daily with dextran sulphate solution. Greater and lesser frequencies may be effective depending upon the individual patient's requirements. It is believed that at least daily treatment would best reduce the risk of P. aeruginosa infection.

It is believed that dextran sulphate may also be effective in assisting with the treatment of patients already infected by P. aeruginosa by reducing the risk of re-colonization of the patient.

Further, it will be appreciated by persons skilled in the art that other, non-topical methods of treatment using dextran sulphate can be successful in reducing the risk of or preventing infection by P. aeruginosa in compromised hosts. It is known that dextran sulphate of average molecular weight of 8,000 is absorbed by the body and circulated systemically. The dextran sulphate may therefore be delivered to sites of P. aeruginosa adhesion and secreted to have effects equivalent to that of the topically applied form. Such methods include systemic therapy, i.e. the ingestion per os of dextran sulphate in tablet form.

The foregoing detailed description and examples are for purposes of illustration only, and are not intended as limiting the scope of the invention. Persons skilled in the art will appreciate the nature and scope of the invention including its practical application.

Dextran

The methodology described below details the experiments performed to determine the effect of dextran on the growth of bacterial cells.

Figure 2:
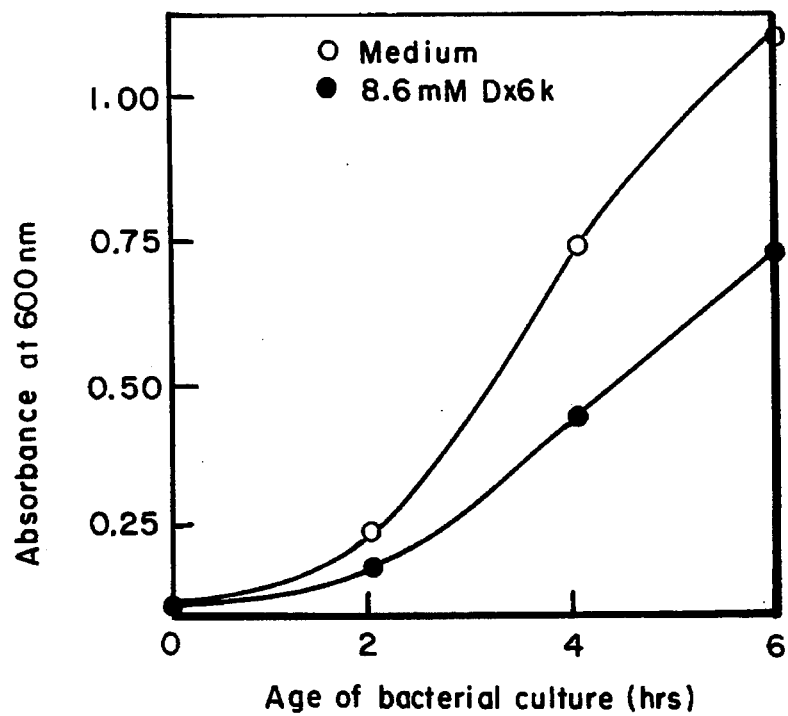
FIG. 2 shows the effect of dextran on the ability of *P. aeruqinosa* to grow in culture.
Figure 3:
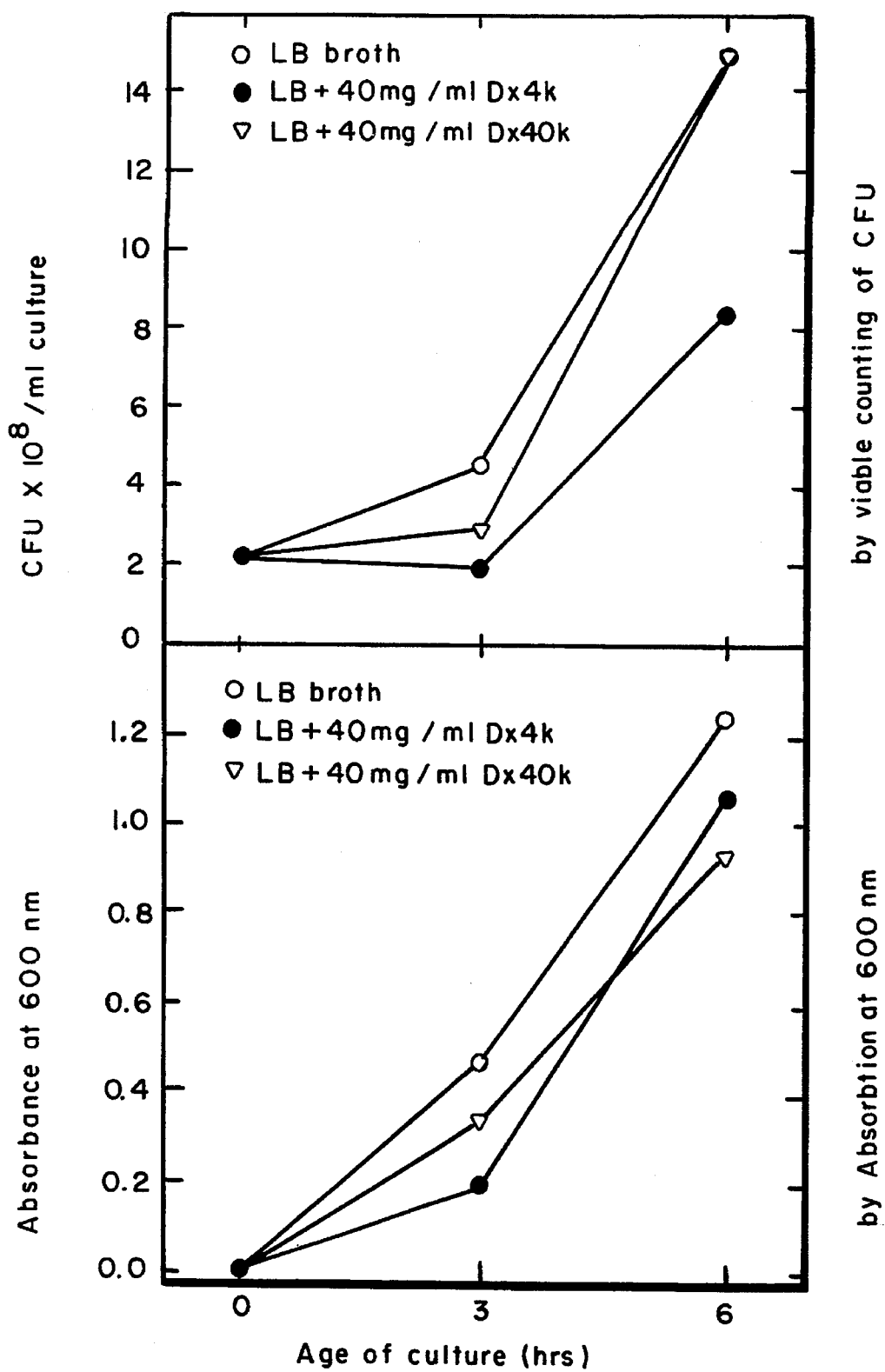
FIG. 3 shows the effect of low molecular weight dextran on the growth of *P. aeruqinosa* in culture.

Bacteria were inoculated into minimal medium (BM2) containing L-methionine and glucose. Alternatively, bacteria were inoculated into LB broth. The bacterial strain inoculated into the LB broth was P. aeruginosa PAK, while the bacterial strain inoculated into the BM2 broth was P. aeruginosa P1. Bacterial growth was monitored by reading the culture absorbency at 600 nm. To test the effect of dextran upon bacterial growth, 8.6 mmol dextran 6,000 (a hydrogenated form of dextran sold under the trademark "Usherdex 6000") was added to the BM2 medium, while 40 mg/ml of either dextran 4,000 (a hydrogenated form of dextran sold under the trademark "Usherdex 4000") or dextran 40,000 was added to the LB broth. These results are shown in FIGS. 2 and 3. In all cases, dextran solutions were adjusted to a pH of between 7.0–7.2 by the addition of 1N NaOH.

Referring to FIG. 2, the open circles represent the growth rate of P. aeruginosa, as measured by a spectrophotometer absorbance reading at 600 nm of the liquid bacterial culture, without the addition of dextran to the bacterial growth medium. The darkened circles represent the growth rate of P. aeruginosa, as measured by a spectrophotometer absorbance reading at 600 nm of the liquid bacterial culture, after the addition of dextran the bacterial growth medium. Comparison of the two growth rates indicates that dextran does not provide a rich growth medium for P. aeruginosa in vitro.

Referring to FIG. 3, upper diagram, the open circles represent the number of colony forming units present in the liquid culture of P. aeruginosa without the addition of dextran the bacterial growth medium. The darkened circles represent the number of colony forming units present in the liquid culture of P. aeruginosa when 40 mg/ml of dextran 4,000 is added to the bacterial growth medium. The open triangles represent the number of colony forming units present in the liquid culture of P. aeruginosa when 40 mg/ml of dextran 40,000 is added to the bacterial growth medium.

Comparison of the number of colony forming units present for any given time when P. aeruginosa is cultured in the absence of dextran to the number of colony forming units present for any given time when P. aeruginosa is cultured in the presence of either dextran 4,000 or dextran 40,000 indicates that neither dextran 4,000 or dextran 40,000 provide a rich growth medium for P. aeruginosa bacterial cells.

Comparison of the number of colony forming units present for any given time when P. aeruginosa is cultured in the presence of dextran 4,000 as opposed to dextran 40,000 indicates that dextran 4,000 has a greater ability than dextran 40,000 to reduce the number of P. aeruginosa bacterial cells which will grow in culture.

Referring to FIG. 3, lower diagram, the open circles represent the number of P. aeruginosa cells present in the liquid culture, as measured by a spectrophotometer absorbance reading at 600 nm of the liquid bacterial culture, present in the liquid culture of P. aeruginosa without the addition of dextran to the bacterial growth medium. The darkened circles represent the number of P. aeruginosa cells present in the liquid culture, as measured by a spectrophotometer absorbance reading at 600 nm of the liquid bacterial culture, when 40 mg/ml of dextran 4,000 is added to the bacterial growth medium. The open triangles represent the number of P. aeruginosa cells present in the liquid culture, as measured by a spectrophotometer absorbance reading at 600 nm of the liquid bacterial culture, when 40 mg/ml of dextran 40,000 is added to the bacterial growth medium.

Comparison of the number of P. aeruginosa cells present in the liquid culture for any given time when P. aeruginosa is cultured in the absence of dextran to the number of P. aeruginosa cells present in the liquid culture for any given time when P. aeruginosa is cultured in the presence of either dextran 4,000 or dextran 40,000, indicates that neither dextran 4,000 and dextran 40,000 provide a rich growth medium for P. aeruginosa bacterial cells.

Comparison of the number of P. aeruginosa cells present in the liquid culture, up to 4.5 hours after the initiation of bacterial growth in the liquid media, when P. aeruginosa is cultured in the presence of dextran 4,000 as opposed to dextran 40,000 indicates that dextran 4,000 has a greater ability than dextran 40,000 to reduce the number of P. aeruginosa bacterial cells which will grow in culture.

The methodology described below was employed in experiments to determine the effects of dextran upon the ability of bacterial cells to adhere to A549 human lung epithelial cells.

A549 human lung epithelial cells were obtained from the American Type Culture Collection (ATCC #CCL 185). The A549 cells were maintained in F-12K medium and harvested by trypsin treatment as recommended by ATCC. Cells were plated at a density of $2 \times 10^4$ cells/well on a coverslip placed in a 24-well tissue culture tray (Becton Dickson, Lincoln Park, N.J.). After 2 hours or 24 hours, cells were washed with PBS (pH 7.0, from Oxoid, Nepean, Ontario, Canada) at 37° C. These were overlaid with 500 µl of Binding Assay Buffer (BAB; 138 mmol NaCl, 8.1 mmol $Na_2HPO_4$, 1.5 mmol $KH_2PO_4$, 2.7 mmol KCl, 1.0 mmol $MgCl_2$, 0.25 mmol $CaCl_2$ and 0.001% phenol red, pH 7.2; Sigma Chemical Company, St. Louis, Mo.). Cells were incubated for 30 minutes at 37° C. in BAB or 10 mmol dextran made in BAB. Subsequently, 25 µl of bacteria (grown in L-broth to $OD_{600}=0.5$) were added and the entire epithelial cell—bacterial cell mixture was re-incubated for another 30 minutes. The coverslips were then washed four times with PBS, fixed in methanol for 15 minutes, mounted on glass microscope slides, dried for 60 minutes at 37° C. and stained for 10 to 15 minutes in Giemsa. Bound bacteria were assessed microscopically by surveying 60 epithelial cells per co-incubation treatment. The average number of bacteria/cell was calculated.

Figure 4:
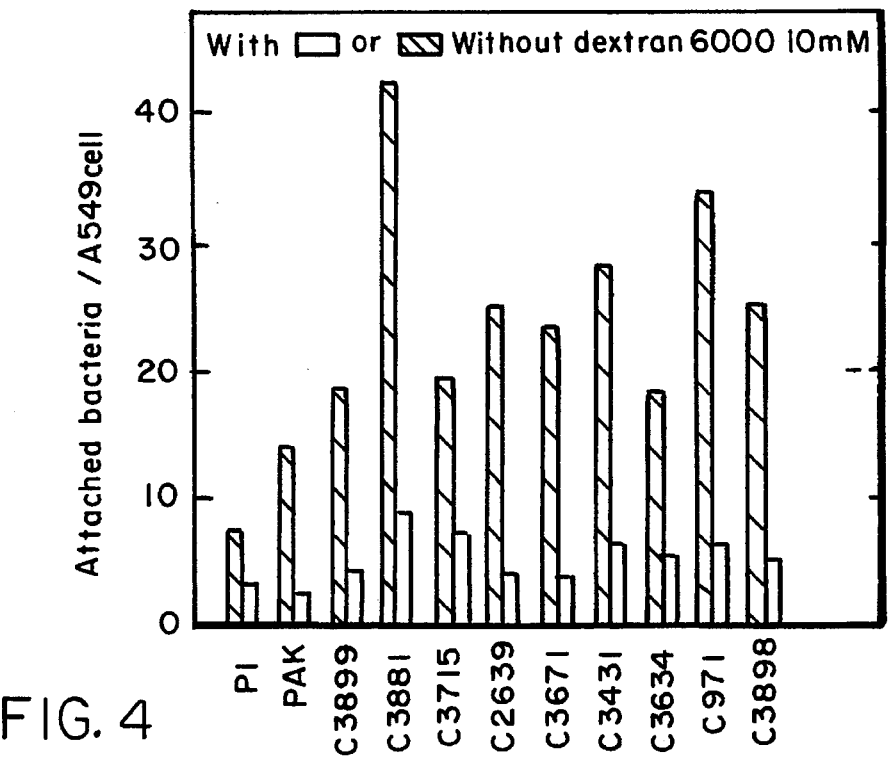
FIG. 4 shows the effect of dextran upon the ability of *P. aeruginosa* isolated from CF patients to adhere to human respiratory epithelial cells.

Referring to FIG. 4, a comparison of the open scale-bars with the closed scale-bars in each column indicates that the addition of the dextran to the culture media caused a reduction of the adhesion of *P. aeruginosa* bacterial cells to the epithelial cells growing in vitro. The results indicate that the reduction in the adhesion of the bacteria was independent of the bacterial isolate. Each bacterial isolate was obtained from a different CF patient (except for strain PAK).

Up to 20 mmol dextran has been used with similar results. A concentration of 10 mmol for dextran 6,000 has been shown to be highly effective at interfering with the adhesion of *P. aeruginosa* to the epithelial cells. Concentrations in the range of 1 mmol to 50 mmol would be useful for the purpose described herein.

Figure 5:
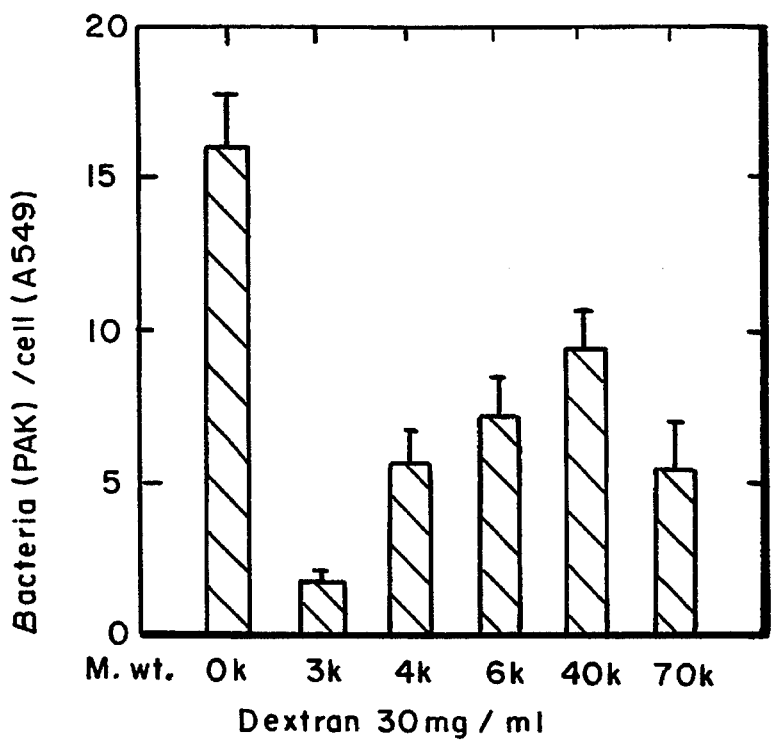
FIG. 5 shows the ability of dextran of various molecular weights to inhibit the adhesion of *P. aeruginosa* PAK to human respiratory epithelial cells.

Referring to FIG. 5, the scale-bars represent the number of bacteria which were observed to adhere to the epithelial cells after 30 minutes of co-incubation of the bacterial and epithelial cells. The addition of dextran to the growth media resulted in a decrease in adherence of *P. aeruginosa* to the epithelial cells. On a comparison of equal weight to volume ratios, dextran 3,000 was most effective in reducing the adhesion of the bacteria to the epithelial cells. The use of dextran with a molecular weight in the range of 3,000 to 1,000,000 would be effective in interfering with the adhesion of *P. aeruginosa* to epithelial cells.

Figure 6:
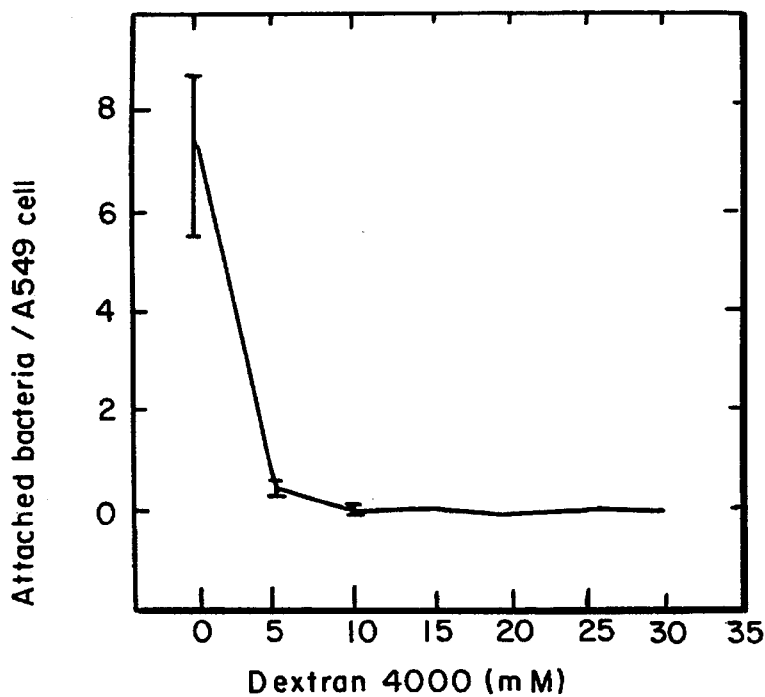
FIG. 6 shows the ability of Dextran 4000 at various concentrations to inhibit the adhesion of *P. aeruginosa* PAK to human respiratory epithelial cells.

Referring to FIG. 6, the results indicate that the addition of dextran 4,000 in concentrations of 5 mmol or greater is highly effective in reducing the adhesion of *P. aeruginosa* to epithelial cells.

Figure 7:
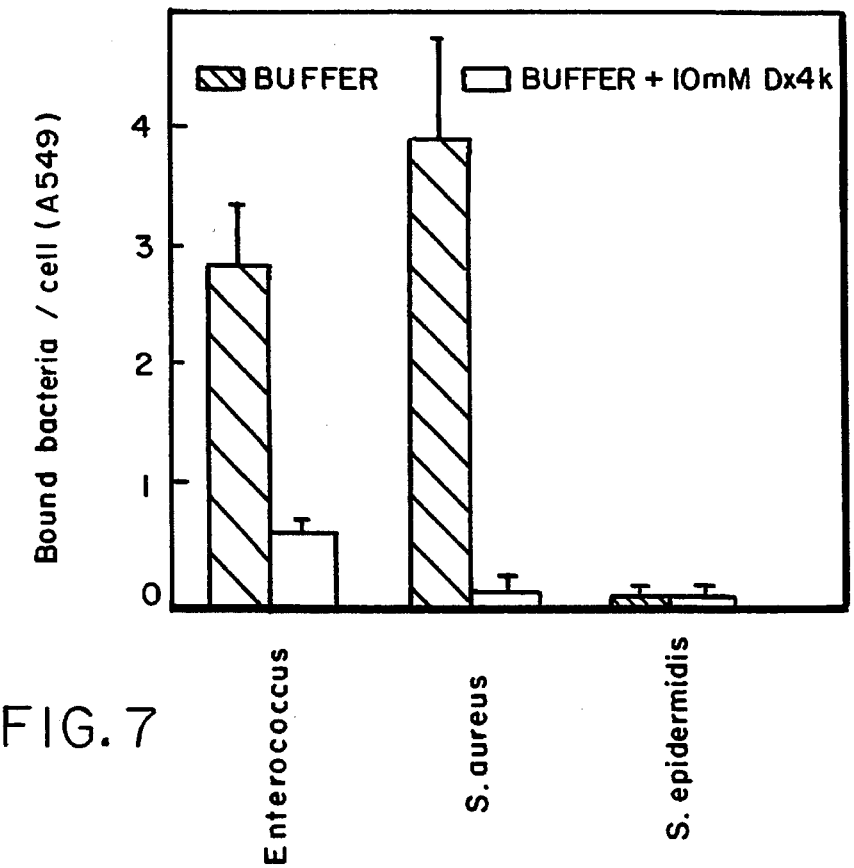
FIGS. 7 and 8 show the effect of Dextran 4000 to inhibit the adhesion of Gram positive bacteria to human respiratory epithelial cells.

Referring to FIG. 7, the darkened scale-bars represent the number of bacteria observed to be adhering to the individual epithelial cells after 30 minutes of co-incubation of the epithelial cells with the bacterium in the absence of dextran. The open scale-bars represent the number of bacteria observed to be adhering to the individual epithelial cells after 30 minutes of co-incubation of the epithelial cells with the bacterium in the presence of 10 mmol dextran 4,000.

For the first and second set of scale-bars, a comparison of the darkened and open scale-bars within each set indicates that the addition of the 10 mmol dextran 4,000 to the culture media during the co-incubation stage is highly effective in reducing the adherence of Gram positive bacteria (Enterococcus and *S. aureus* respectively) to the epithelial cells. The third set of scale-bars indicates that *Staphylococcus epidermidis*, a Gram positive bacteria, did not bind to the epithelial cells even in the absence of dextran.

Figure 8:
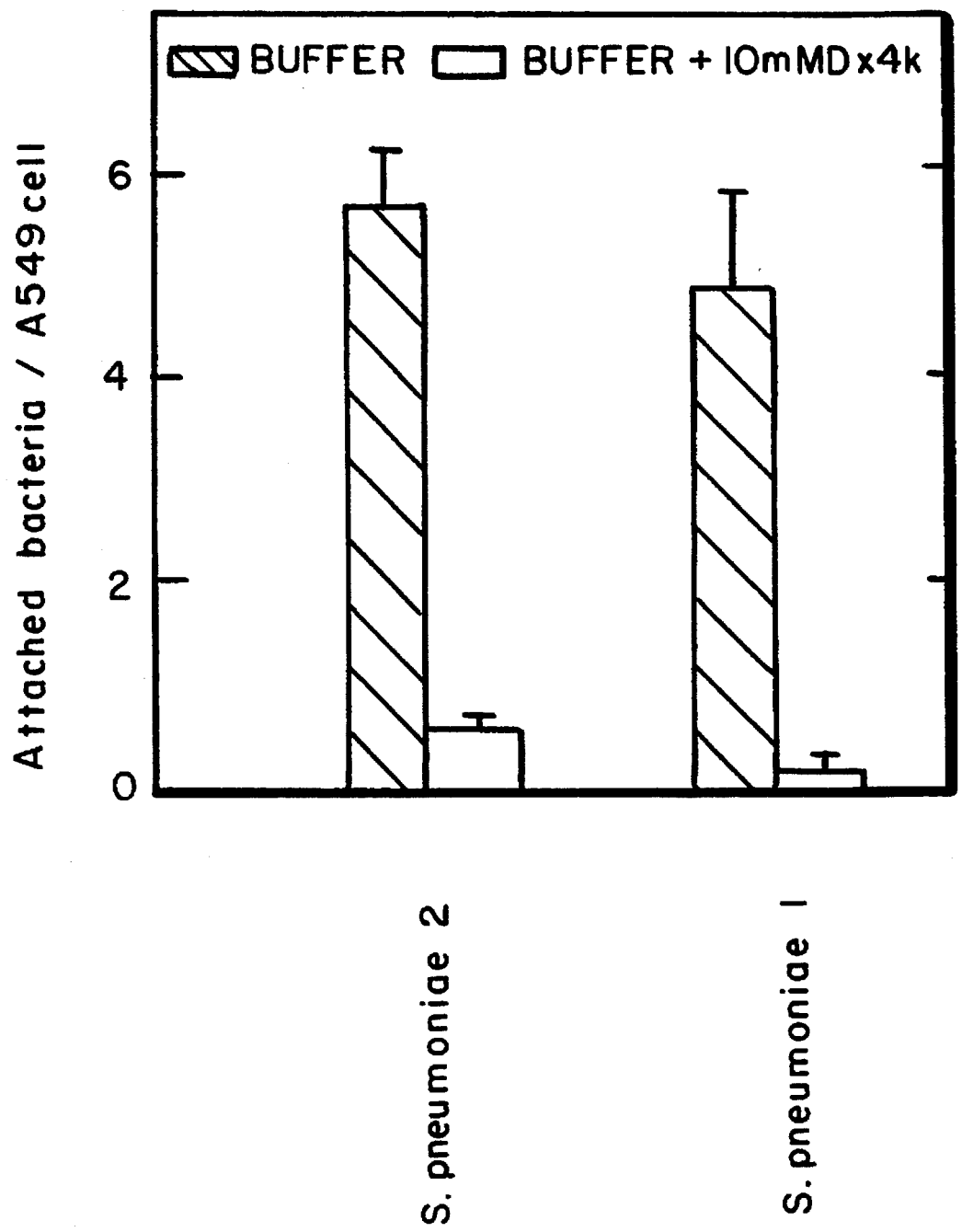

Referring to FIG. 8, the darkened scale-bars represent the number of bacteria observed to be adhering to the individual epithelial cells after 30 minutes of co-incubation of the epithelial cells with the bacterium in the absence of dextran. The open scale-bars represent the number of bacteria observed to be adhering to the individual epithelial cells after 30 minutes of co-incubation of the epithelial cells with the bacterium in the presence of 10 mmol dextran 4,000.

For each strain of *Streptococcus pneumoniae* tested, a comparison of the darkened and open scale-bars within each set indicates that the addition of the 10 mmol dextran 4,000 to the culture media during the co-incubation stage is highly effective in reducing the adherence of Gram positive bacteria to the epithelial cells.

In vivo, dextran would preferably be administered topically. Dextran as the active ingredient may be administered topically by gargle, swish and swallow, oral lozenge, aerosol or other such manner. Dextran and suitable carrier compositions will be understood by those skilled in the art.

Preferably, dextran is delivered to the site of potential adhesion to buccal or respiratory epithelial cells in concentrations as mentioned above.

Although the foregoing description suggests specific manners of topical administration of dextran to buccal or respiratory epithelial cells, it will be understood by persons skilled in the art that other methods of administration are possible.

The dextran used in the present experiments was in its hydrogenated form. It is expected that dextran in its unhydrogenated form would also be effective for use in a treatment to reduce the risk of the type of bacterial infections described herein.

Preferably, a patient would be treated 2–3 times daily with dextran solution. Greater and lesser frequencies may be effective depending upon the individual patient's requirements. It is believed that at least daily treatment would best reduce the risk of *P. aeruginosa* infection.

It is believed that dextran may also be effective in assisting with the treatment of patients already infected by *P. aeruginosa* by reducing the risk of re-colonization of the patient.

Further, it will be appreciated by persons skilled in the art that other, non-topical methods of treatment using dextran can be successful in reducing the risk of or preventing infection by *P. aeruginosa* in compromised hosts. It is known that dextran of average molecular weight is absorbed by the body and circulated systemically. The dextran may therefore be delivered to sites of *P. aeruginosa* adhesion and secreted to have effects equivalent to that of the topically applied form. Such methods include systemic therapy, i.e. the ingestion per os of dextran in tablet form.

The foregoing detailed description and examples are for purposes of illustration only, and are not intended as limiting the scope of the invention. Persons skilled in the art will appreciate the nature and scope of the invention including its practical application.

We claim:

1. A method for reducing the risk of respiratory system infection by bacterial pathogens which comprises administering to a patient in need of such treatment a pharmaceutical composition comprising an effective amount of dextran in admixture with a pharmaceutically acceptable diluent or carrier.

2. The method of claim 1 wherein said dextran is hydrogenated.

3. The method of claim 2 wherein said carrier is a liquid, an oral lozenge or an aerosol.

4. The method of claim 3 wherein said dextran is administered in liquid form by gargle or swish and swallow.

5. The method of claim 3 wherein said dextran is present in a final concentration of about 1–50 mmol.

6. The method of claim 5 wherein said dextran is present in a final concentration of about 10–20 mmol.

7. The method of claim 6 wherein said dextran is present in a final concentration of about 10 mmol.

8. The method of claim 3 wherein said dextran concentration at a potential site of bacterial pathogen adhesion is about 10–20 mmol.

9. The method of claim 8 wherein said dextran concentration at a potential site of bacterial pathogen adhesion is about 10 mmol.

10. The method of claim 3 wherein said bacterial pathogen is *Pseudomonas aeruginosa, Staphylococcus epidermidis, Staphylococcus aureus, Streptococcus pneummoniae* or Enterococcus.

11. The method of claim 2 wherein said dextran has an average molecular weight of about 3,000–1,000,000.

12. The method of claim 10 wherein said dextran has an average molecular weight of about 4,000–6,000.

13. The method of claim 11 wherein dextran has an average molecular weight of about 4,000.

14. A method for reducing adhesion of bacterial pathogens to buccal or respiratory epithelial cells in vivo which comprises administering to a patient in need of such treatment a pharmaceutical composition comprising an effective amount of dextran in admixture with a pharmaceutically acceptable diluent or carrier.

15. The method of claim 14 wherein said bacterial pathogens are *Pseudomonas aeruginosa, Staphylococcus epidermidis, Staphylococcus aureus, Streptococcus pneumoniae* or *Enterococcus*.

16. The method of claim 14 wherein said bacterial pathogen is *Pseudomonas aeruginosa* and said patient has cystic fibrosis.

17. A method for reducing the risk of respiratory tract infection by *Pseudomonas aeruginosa* in a patient having cystic fibrosis which comprises administering to said patient a pharmaceutical composition comprising an effective amount of dextran in admixture with a pharmaceutically acceptable diluent or carrier.

* * * * *